United States Patent [19]

Takagawa et al.

[11] Patent Number: 5,527,977
[45] Date of Patent: Jun. 18, 1996

[54] PROCESS FOR PRODUCING MONOALKENYL AROMATIC HYDROCARBON COMPOUND

[75] Inventors: Makoto Takagawa; Kenichi Nakamura; Kinji Kato; Akio Hashimoto; Takayo Sasaki, all of Tsukuba, Japan

[73] Assignee: Mitsubishi Gas Chemical Company, Inc., Tokyo, Japan

[21] Appl. No.: 266,145

[22] Filed: Jun. 27, 1994

[30] Foreign Application Priority Data

Jul. 29, 1993 [JP] Japan ................................. 5-188215
Jul. 29, 1993 [JP] Japan ................................. 5-188216
Jul. 29, 1993 [JP] Japan ................................. 5-188217

[51] Int. Cl.$^6$ ............................................. C07C 2/72
[52] U.S. Cl. ..................... 585/452; 585/435; 585/446; 585/467; 585/802
[58] Field of Search ............................ 585/446, 452, 585/453, 467, 435, 438, 802

[56] References Cited

U.S. PATENT DOCUMENTS

| | | | |
|---|---|---|---|
| 3,244,758 | 4/1966 | Eberhardt | 260/668 |
| 5,334,794 | 8/1994 | Fushimi et al. | 585/452 |
| 5,344,806 | 9/1994 | Fushimi et al. | 585/452 |
| 5,347,062 | 9/1994 | Fukao et al. | 585/452 |
| 5,367,098 | 11/1994 | Fushimi et al. | 585/452 |

FOREIGN PATENT DOCUMENTS 0676544 12/1963 Canada.
0173335 3/1986 European Pat. Off..
A-0547336 6/1993 European Pat. Off..

OTHER PUBLICATIONS

Database WPI, Week 9327, Derwent Publications Ltd., London, GB; AN 93–216687 of JP–A–05 140 006 (Teijin Ltd.), 1993.
Database WPI, Week 8226, Derwent Publications Ltd., London, GB; AN 76–29239 of JP–A–57 026 489, 1982.
Database WPI, Week 7442, Derwent Publications Ltd., London, GB; AN 74–73518 of JP–A–49 070 929, 1974.

*Primary Examiner*—Ponnathapura Achutamurthy
*Attorney, Agent, or Firm*—Frishauf, Holtz, Goodman, Langer & Chick

[57] ABSTRACT

Their is disclosed a process for producing a monoalkenyl aromatic hydrocarbon compound (e.g. 5-(o-tolyl)-2-pentene) which comprises the steps of alkenylating a side chain of an aromatic hydrocarbon compound having at lease one hydrogen atom bonded to α-position of the side chain (e.g. alkylbenzene) by the use of a conjugated diene having 4 to 5 carbon atoms (e.g. 1-3 butadiene) in the presence an alkali metal-based catalyst supported on a carrier; removing at least part of the catalyst from the resultant reaction product by separating the same; inactivating and optionally removing the catalyst contained in the reaction product; and thereafter distilling the reaction produce in liquid form to separate and recover the objective monoalkenyl aromatic hydrocarbon compound. By virtue of using the above specific method, the process can prevent the change in quality and properly of the objective product even during atmospheric distillation, produce the objective product with high purity in high recovery race and operate a distillation column during a long stable period of time.

42 Claims, No Drawings

PROCESS FOR PRODUCING MONOALKENYL AROMATIC HYDROCARBON COMPOUND

BACKGROUND OF THE INVENTION

1. Field of the Invention

The present invention relates to a process for producing a monoalkenyl aromatic hydrocarbon compound. More particularly, it pertains to a process for producing a monoalkenyl aromatic hydrocarbon compound by alkenylating a side chain of an aromatic hydrocarbon compound having at least one hydrogen atom bonded to an $\alpha$-position of the side chain by using a conjugated diene having 4 or 5 carbon atoms in the presence of an alkali metal-based catalyst, and separating the objective monoalkenyl aromatic hydrocarbon compound in the reaction product to recover the same with high purity in a high recovery rate.

2. Description of Related Arts

As a catalyst for producing a monoalkenyl aromatic hydrocarbon compound by alkenylating a side chain of an aromatic hydrocarbon compound by using a conjugated diene having 4 or 5 carbon atoms, there is known a catalyst comprising an alkali metal such as sodium and potassium or an alloy thereof.

It is known that in the case where the objective monoalkenyl aromatic hydrocarbon compound is recovered by separation from the reaction product in liquid form obtained by the use of such a catalyst, an attempt to separate and recover the objective monoalkenyl aromatic hydrocarbon compound after the completion of the reaction by allowing the reaction product to cool, separating the liquid phase containing the objective product from the catalyst through decantation or filtration, and distilling the separated liquid phase results in failure to obtain the objective monoalkenyl aromatic hydrocarbon compound with high purity in high yield, since the objective compound changes in quality and properties during such steps. In order to solve such a problem there are proposed various methods for treating the reaction mixture.

There is proposed in Japanese Patent Application Laid-Open No. 4127/1976, a method in which the concentration of the total amounts of alkali metals and organic alkali metal compounds in the hydrocarbon compound to be used as the starting raw material for distillation is set to the range of 0.09 to 15 mg-atom expressed in terms of alkali metal components per one (1) kg of the hydrocarbon compound. In the above-mentioned method, however, it does not follow that all the alkali metal catalyst components are removed, but part of the components are inevitably mixed in the liquid phase in the form of a soluble alkyl compound or an alkenyl complex. In the case of the reaction product being introduced as it is into a distillation column in the method, it occurs that the monoalkenyl aromatic hydrocarbon compound further reacts with itself or with an unreacted alkylaromatic hydrocarbon compound to form a high molecular byproduct owing to the coexistence of the active catalyst. The objective product is converted to the alkylaromatic hydrocarbon compound as the starting raw material by the reverse reaction, or an isomer other than the objective monoalkenyl aromatic hydrocarbon compound is formed by the transfer of the double bond. Even if the concentration of the total amounts of alkali metals and organic alkali metal compounds are lowered, the change in quality and properties of the objective compound can be lessened to some extent, but can not be entirely prevented. When the distillation column is operated for a long period of time, the alkali metals and organic alkali metal compounds each in a slight amount are concentrated in the distillation column, finally making it impossible to obtain the objective monoalkenyl aromatic hydrocarbon compound with high purity and lowering the recovery rate.

The change in quality and properties of the objective compound can be suppressed to some extent by lowering the distillation temperature, which however, makes it necessary to carry out the distillation under reduced pressure. In order to completely eliminate the change in quality and property of the objective monoalkenyl aromatic hydrocarbon compound, the above-mentioned method requires a high vacuum and accordingly, it is far from an industrially economical process.

There is proposed in Japanese Patent Application Laid-Open No. 70929/1974, a method in which the catalyst is removed by separating it from the reaction product. Subsequently the resultant reaction liquid is treated with carbon dioxide, followed by distillation or. Alternatively, the reaction product is treated with carbon dioxide and then, the catalyst is removed by separating it from the reaction product, followed by distillation. The aforesaid method can prevent the change in quality and properties of the objective monoalkenyl aromatic hydrocarbon compound in the course of distillation since the alkali metal and organic alkali metal compound are completely inactivated by the carbon dioxide treatment. However, this method brings about the disadvantage that some of the formed alkali salts such as alkali carbonates and alkali carboxylates that are soluble in organic solvents are introduced into a distillation column, where the unreacted aromatic hydrocarbon is distilled away, and the alkali salts beyond this solubilities are precipitated and accumulated in solid form inside the distillation column, thereby lowering the gas-liquid contact efficiency and distillation efficiency in the distillation column and finally making it impossible to proceed with the distillation procedure because of clogging in the column. That is to say, unless the alkali metal components are completely removed from the system, it is impossible to operate the distillation column in a stable manner and obtain the objective monoalkenyl aromatic hydrocarbon compound with high purity.

There is proposed in Japanese Patent Publication No. 26489/1982, a method in which an alkenyl aromatic hydrocarbon compound is brought into contact with water and the pH of the water phase is adjusted to 6 or less to make the alkali metal catalyst water-soluble, followed by separation of the catalyst. However, the above-mentioned method involves the danger of causing fire in addition to the generation of a large amount of reaction heat in the case of bringing the reaction product into contact with water. Although it is possible to control the reaction to some extent by regulating the amount of water or reaction product in liquid form to be brought into contact, such treatment requires a long period and a large-scale equipment when carried out on industrial scale and proves unpractical.

In U.S. Pat. No. 3,244,758, the occurrence of an unfavorable side reaction in the course of distillation is prevented by inactivating the alkali metals and alkali metal compounds contained in the reaction product in liquid form through the addition of isopropanol prior to distillation. Although the aforesaid method can avoid the danger of causing fire in addition to the generation of a large amount of reaction heat in the case of contact between the reaction product with water as mentioned above, but the inactivated alkali metal catalyst in the form of an alkali metal alcoholate which is soluble in organic solvents is introduced into a distillation column, thus unfavorably causing the problem as is the case with the foregoing.

As described hereinbefore, there has not yet been discovered any suitable method for removing alkali metal components in the reaction product when an alkali metal or an alloy thereof is employed as a catalyst in the alkenylation reaction.

On the other hand, it has been found that an alkali metal supported on a carrier other than the above-described alkali metals or alloys thereof is effective as a catalyst for alkenylation reaction. It has also been found that among various alkali metal catalysts each supported on a carrier, the catalysts prepared by the treatment as described hereunder exhibits not only extremely high activity in alkenylation reaction but also remarkably low inflammability. Specifically, the above-mentioned high activity and low inflammability are assured by the use of the carrier obtained by calcining a mixture of potassium hydroxide and aluminum hydroxide; the carrier obtained by calcining the mixture of a basic potassium compound and alumina; the alkaline earth metaloxide carrier containing a potassium compound; the zirconium oxide carrier containing a potassium compound; or the alkali metal-based catalyst supported on a carrier obtained by heat treating any of the aforesaid carriers along with metallic sodium in an atmosphere of an inert gas. However, there has not been, in fact, proposed a treatment method in the case of employing the above-mentioned alkali metal-based catalyst supported on a carrier.

Under such a circumstance, an attempt was made by the present inventors to recover a monoalkenyl aromatic hydrocarbon compound by method the following. The reaction product obtained by the use of the aforestated alkali metal-based catalyst supported on a carrier is allowed to stand and be filtered to separate the liquid phase containing the objective product from the catalyst, and the resultant reaction liquid is distilled to separate the objective product. As a result, it was impossible to obtain the objective monoalkenyl aromatic hydrocarbon compound with high purity in high recovery rate, since the objective compound changed in quality and properties during the course of distillation. In addition, insoluble compounds were accumulated in the distillation column. As a result, the column was clogged by the accumulated mater and thus it was impossible to continue with the distilling (distillation) operation the column.

That is to say, it was impossible to completely remove the catalyst in the form of fine particles by allowing the reaction product to stand, followed by filtration, and part of the alkali metal is mixed in the liquid phase as a soluble alkyl or alkenyl complex. When the reaction product containing such a complex is introduced as it is in a distillation column, the coexisting active catalyst causes the monoalkenyl aromatic hydrocarbon compound to further react with itself or with an unreacted alkyl hydrocarbon compound resulting in the formation of a high molecular byproduct, which is converted by reverse reaction into the alkyl aromatic hydrocarbon compound, i.e., the starting raw material, or to form an isomer other than the objective monoalkenyl aromatic hydrocarbon compound by the transfer of the double bond. Consequently, it is impossible to produce the objective monoalkenyl aromatic hydrocarbon compound with high purity, and the recovery rate is lowered.

The change in quality and properties of the objective monoalkenyl aromatic hydrocarbon compound can be suppressed to some extent by lowering the distillation temperature as mentioned hereinbefore, which however, necessitates to performing the distillation under reduced pressure. In order to completely eliminate the change in quality and properties of the objective compound, the above-mentioned low temperature method requires a high vacuum and thus, it is far from industrially practical because of the expensiveness in equipment and operation.

Moreover, some alkali metals in the form of alkali salts that are soluble in organic solvents are introduced in a distillation column, where the unreacted aromatic hydrocarbon is distilled away, and the alkali salts beyond their solubilities are precipitated and accumulated in solid form inside the distillation column, thereby lowering the gas-liquid efficiency and distillation efficiency in the column and finally making it impossible to proceed with the distillation procedure because of clogging in the column. Thus the above-mentioned problem can not be avoided by running conditions only at the time of distillation.

SUMMARY OF THE INVENTION

It is a primary object of the present invention to provide a process for producing a monoalkenyl aromatic hydrocarbon compound with high purity in high recovery rate by alkenylating a side chain of an aromatic hydrocarbon compound having at least one hydrogen atom bonded to an $\alpha$-position of the side chain by the use of a conjugated diene having 4 to 5 carbon atoms in the presence of an alkali metal-based catalyst supported on a carrier; and recovering the resultant monoalkenyl aromatic hydrocarbon compound by separating the same from the resultant reaction product.

Under such circumstances, intensive research and investigation were continued by the present inventors in order to develop a process for producing a monoalkenyl aromatic hydrocarbon compound by alkenylating a side chain of an aromatic hydrocarbon compound having at least one hydrogen atom bonded to an $\alpha$-position of the side chain by the use of a conjugated diene having 4 to 5 carbon atoms in the presence of an alkali metal-based catalyst supported on a carrier; and recovering the resultant monoalkenyl aromatic hydrocarbon compound by separating the same from the resultant reaction product. As a result, it has been found that a monoalkenyl aromatic hydrocarbon compound with high purity can be produced in high recovery rate by a method in which the reaction product in liquid form from which most of the catalyst has been removed by sedimentation is brought into contact with a specific solid, liquid or gas to inactivate and/or remove the alkali metal-based catalyst and then the reaction product thus treated is distilled to separate and recover the objective product. The present invention has been accomplished on the basis of the aforestated finding.

Specifically the present invention provides a process for producing a monoalkenyl aromatic hydrocarbon compound which comprises the steps of alkenylating a side chain of an aromatic hydrocarbon compound having at least one hydrogen atom bonded to an $\alpha$-position of the side chain by the use of a conjugated diene having 4 to 5 carbon atoms in the presence of an alkali metal-based catalyst supported on a carrier; removing at least part of said catalyst from the resultant reaction product by separating the same; inactivating or, inactivating and removing, the catalyst contained in the reaction product; and thereafter distilling the reaction product in liquid form to separate and recover the objective monoalkenyl aromatic hydrocarbon compound, said inactivation or inactivation/removal being effected by bringing the reaction liquid into contact preferably with at least one member selected from the group consisting of a solid acid, a carbonaceous material and a cationic ion exchange resin; with at least one member selected from the group consisting of air, oxygen, steam and carbon dioxide; with a mixed gas of at least one member selected from the group consisting of oxygen, steam and carbon dioxide with a diluting inert gas; with at least one member selected from the group consisting of water and a solution of an acid in water; with an alcohol and thereafter with at least one member selected from the group consisting of water and a solution of an acid in water; or with an alcohol and thereafter with at least one member selected from the group consisting of a solid acid, a carbonaceous material and a cationic ion exchange resin.

DESCRIPTION OF PREFERRED EMBODIMENTS

Examples of the specific aromatic hydrocarbon compound having at least one hydrogen atom bonded at an α-position of the side chain to be employed as the starting raw material in the present invention include monocyclic aromatic hydrocarbons such as monoalkylbenzenes, for example, toluene; ethylbenzene; n-propylbenzene; isopropylbenzene; n-butylbenzene; sec-butylbenzene; and isobutylbenzene, dialkylbenzenes enumerated by o-, m- and p-xylene; o-, m- and p-ethyltoluenes; and o-, m- and p-diethylbenzenes, trialkylbenzenes, for example, mesitylene; and pseudocumene and polyalkylbenzenes, for example, by 1,2,3,5-tetramethylbenzene; 1,2,4,5-tetramethylbenzene; pentamethylbenzene; and hexamethylbenzene, and polycyclic aromatic hydrocarbons such as 1- and 2-methylnaphthalene, dimethylnaphthalenes, tetrahydronaphthalenes and indanes.

As the conjugated dienes having 4 or 5 carbon atoms as another starting raw material, there are preferably used 1,3-butadiene; 1,3-pentadiene; and isoprene.

As the alkali metal-based catalyst supported on a carrier to be used in the process according to the present invention, there is employed metallic potassium and/or metallic sodium each supported on a carrier as a catalyst. Examples of the catalysts or carriers that are suitable in view of activity and safety include a carrier obtained by calcining the mixture of potassium hydroxide and aluminum hydroxide at 400° to 700° C., a carrier obtained by calcining the mixture of a basic potassium compound and alumina at 500° to 700° C., an alkaline earth metal oxide carrier containing a potassium compound, and a zirconium oxide carrier containing a potassium compound, e.g., a catalyst comprising a mixture obtained by adding metallic sodium to any of the abovementioned carriers and heat treating the mixture preferably at 100° to 300° C., in an atmosphere of an inert gas.

In employing the catalyst thus obtained in the alkenylation reaction, various reaction systems are available. In general, the selectivity to the objective monoalkenyl aromatic hydrocarbon compound can preferably be enhanced by the system wherein an aromatic hydrocarbon compound as one of the staring raw materials is allowed to be present in excess over a conjugated diene. For the purpose of enhancing the selectivity, a semi-batchwise system is preferable in which a conjugated diene is continuously fed into the reaction system. In the case of continuous reaction by a complete mixing system or a flow system through a fixed bed, it is preferable for enhancing the selectivity to adopt the reaction system capable of lowering the concentration of a conjugated diene in the reactor such as the system in which a conjugated diene is fed into each stage of a multistage reactor to be adopted.

The reaction temperature in the process according to the present invention is in the range of preferably 100° to 200° C. A temperature lower than the above lower limit can cause the reaction to take place, but results in failure to attain a sufficient reaction rate; and besides it tends to lower the selectivity, while a temperature that higher than the above higher limit unfavorably leads to an increased amount of a byproduct such as tar components. The alkenylation reaction in the process according to the present invention is carried out under the conditions in which the aromatic hydrocarbon compound as the starting raw material and the objective product are substantially in the form of liquid.

The reaction pressure is not specifically limited insofar as the aromatic hydrocarbon compound as the starting raw material and the objective product are present substantially in the form of liquid. It is in the range of 0.05 to 5 absolute atmospheric pressure ($0.05 \times 10^5$ to $5.07 \times 10^5$ Pa), preferably 0.1 to 2 absolute atmospheric pressure ($0.10 \times 10^5$ to $2.03 \times 10^5$ Pa).

In the process according to the present invention, the molar ratio of the conjugated diene having 4 to 5 carbon atoms as another starting raw material to the aromatic hydrocarbon compound as a starting raw material is generally 0.01 to one (1), preferably 0.03 to 0.5. A molar ratio thereof higher than the above higher limit unfavorably causes an increase in the formation of the compound in which the monoalkenyl aromatic hydrocarbon compound thus produced is further reacted with the excess diene to allow the addition of at least two molecules of the diene to one molecule of the aromatic hydrocarbon compound and the likelihood of diene polymerization, whereby the selectivity to the objective compound is undesirably worsened.

The amount of the catalyst to be used in the process according to the present invention is 0.01% or more, preferably 0.05% or more by weight based on the amount of the aromatic hydrocarbon compound as a starting raw material.

As described hereinbefore, the reaction system is selected from a batchwise system, a semi-batchwise system, a complete mixed flow system and the like in putting the process of the invention into practice. There is usually adopted 0.1 to 10 hours as the reaction time in a batchwise and a semi-batchwise system and as the retention time in a complete mixing system. In the case of a flow system through a fixed bed, the liquid hourly space velocity (LHSV) for the aromatic hydrocarbon compound in the range of 0.1 to 10 $h^{-1}$ is usually selected.

In the case of carrying out the reaction with a suspended catalyst, it is preferable that, first of all, the reaction product in the form of liquid be allowed to stand, and at least a part, preferably most of the catalyst be sedimented to remove the same. Subsequently, the reaction product in liquid form is taken out from the reactor, followed by treatment.

The reaction product thus taken out contains a part of the catalyst in the form of fine grains. Even if such catalyst is removed by filtering it with a filter, part of the alkali metal in the form of a soluble alkyl-or-alkenyl complex or a soluble alkali salt is mixed in the liquid phase. In the case where the reaction product in liquid form containing such alkali metal is introduced as it is into a distillation column, the soluble active catalyst present in the reaction product causes the monoalkenyl aromatic hydrocarbon compound to change in the quality and properties. In spite of a relatively low concentration of the soluble catalyst, the change in the quality and properties of the monoalkenyl aromatic hydrocarbon compound is significantly increased during a long-term running wherein the soluble catalyst is concentrated in the holdup in the distillation column. In view of the above fact, the soluble active catalyst needs to be inactivated prior to the introduction of the reaction product into the distillation column.

As a method for inactivating the soluble catalyst, there are available a method in which the reaction product is filtered with a filter to remove most of the alkali metal-based catalyst supported on a carrier, followed by inactivation and a method in which the reaction product is inactivated as such. Although any of the aforesaid methods is usable, the use of the former method is disadvantageous in that the active alkali metal-based catalyst collected on the filter causes the monoalkenyl aromatic hydrocarbon compound to change in the quality and properties on the filter to form a high molecular polymer of the monoalkenyl aromatic hydrocarbon compound, which sometimes brings about clogging of the filter. Thus, in the present invention the latter method is preferably used, in which after the catalyst is inactivated, part of the alkali metal-based catalyst supported on a carrier in the form of fine grains is contained in the reaction product. It is preferable but is not always necessary to remove the fine grains with a filter, since the quantity of fine grains varies depending on the treatment method. A filter, when used, has preferably a pore sizes of 5 micron or smaller. The present invention can use a method for inactivating the catalyst which include the following: (1) a method in which the reaction product is brought into contact with at least one member selected from the group consisting of a solid acid, a carbonaceous material and a cationic ion exchange resin; (2) a method in which it is brought into contact with at least one member selected from the group consisting of air, oxygen, steam and carbon dioxide; (3) a method in which it is brought into contact with a mixed gas of at least one member selected from the group consisting of oxygen, steam and carbon dioxide with a diluting inert gas; (4) a method in which it is brought into contact with at least one member selected from the group consisting of water and a solution of an acid in water; (5) a method in which it is brought into contact with an alcohol and thereafter with at least one member selected from the group consisting of water and a solution of an acid in water; (6) a method in which it is brought into contact with an alcohol and thereafter with at least one member selected from the group consisting of a solid acid, a carbonaceous material and a cationic ion exchange resin; and (7) a method in which at least two methods mentioned above are combined. By any of the above-mentioned methods, the catalyst in the reaction liquid is inactivated, and the alkenyl aromatic hydrocarbon compound is prevented from changing in properties even when the treated reaction liquid is subjected to distillation.

In the following, the above-mentioned treatment method will be described in more detail.

In the case of adopting a method in which the reaction product, from which at least a part of catalyst in it has been removed, is brought into contact with a solid acid, the active alkali metal component in the alkali metal-based catalyst supported on a carrier is adsorbed onto the solid acid and can be inactivated and/or removed by acid-base reaction. Examples of preferably usable solid acids in the present invention include activated clay, alumina, silica-alumina and various types of zeolites, of which hydrogen ion exchange type zeolite is particularly suitable, however, the type of zeolite is not specifically limited but may be any of type Y, type X, type ZSM and ferrierite.

In the case of adopting a method in which the reaction product is brought into contact with a carbonaceous material, the active alkali metal component in the alkali metal-based catalyst supported on a carrier is adsorbed mainly onto the functional groups such as surface hydroxy group and carboxyl group of the carbonaceous material or occluded in the material by an intercalation mechanism, and thereby can be inactivated and/or removed. Examples of usable carbonaceous material in the present invention include graphite, activated carbon, amorphous carbon obtained by baking petroleum-based or coal-based pitch and PAN-based carbon fiber without specific limitation. Each of the carbonaceous materials can be calcined, oxidized or regulated in the degree of carbonization, surface functional group, surface area or the like as required prior to actual use.

In the case of adopting a method in which the reaction product is brought into contact with a cationic ion exchange resin, the active alkali metal component in the alkali metal-based catalyst supported on a carrier is adsorbed onto the functional group on the cationic ion exchange resin by acid-base reaction, and thereby can be inactivated and/or removed. Examples of usable cationic ion exchange resin in the present invention include that of sulfonic acid type and that of carboxylic acid type, and that having a high degree of crosslinking is preferably employed from the viewpoint of swell characteristics.

The method of bringing the reaction product into contact with any of the above-mentioned solids is not specifically limited insofar as the solid-liquid contact is sufficient, but may be selected from a batchwise system, a semi-batchwise system, a flow system through fixed a bed and the like. Of these systems, a flow system through a fixed bed is preferable from the standpoint of industrial operation in that the slight quantity of fine grains remaining in the reaction liquid can be adsorbed onto the solid by passing the reaction liquid through the packed bed of the solid. The solid-reaction liquid contact method is usually free from substantial heat generation and is enhanced in safety. In case of danger of fire due to substantial heat generation, heat generation can easily be controlled by controlling the feed rate of the solid or reaction liquid. There is adoptable in the present invention, a method in which the reaction liquid is brought into contact with a gas such as air, oxygen, steam, mixed gas of carbon dioxide and oxygen or mixed gas of carbon dioxide and steam, ore a liquid such as water, aqueous solution of an acid or alcohol to inactivate in advance to some extent, the active alkali metal-based catalyst supported on a carrier and subsequently the reaction liquid is brought into contact with the above-mentioned solid to completely inactivate and/or remove the catalyst.

The contact temperature at the time of bringing the reaction liquid into contact with the aforesaid solid can be selected in a wide range from room temperature to the boiling point of the aromatic hydrocarbon compound as the starting raw material, but room temperature is usually sufficient. The amount of the solid to be employed is not specifically limited, but may be an amount sufficient for removing the alkali metal components. Likewise, the contact time is not specifically limited, but may be a period of time sufficient for inactivating and/or removing the active alkali metal-based catalyst supported on a carrier. The LSV in the case of adopting the flow system through the fixed bed may be determined taking into consideration the desired retention time and the size of an adsorption column without specific limitation, but is preferably 0.05 to 50 $h^{-1}$ for the ordinary reaction liquid.

In the present invention, the catalyst can be inactivated and/or removed by bringing the reaction product from which at least a part of catalyst in it has been removed in liquid form into contact with at least one member selected from the group consisting of air, oxygen, steam and carbon dioxide or with a mixed gas of at least one member selected from the group consisting of oxygen, steam and carbon dioxide with a diluting inert gas such as nitrogen, helium or argon. Of these, specific examples of the usable gas include air, oxygen, steam, carbon dioxide, steam-containing inert gas, oxygen-containing inert gas, mixed gas of carbon dioxide with air, mixed gas of carbon dioxide with oxygen and mixed gas of carbon dioxide with steam.

As a method for using the above-mentioned gas, there is available an extremely convenient method in which the gas is brought into contact sufficiently with the reaction liquid by blowing the gas thereinto to inactivate the active alkali metal-based catalyst supported on a carrier into the oxide, hydroxide or carbonate or the like of the alkali metal. Any of the above-exemplified gases are usable, of which are industrially preferable air, steam-containing air, mixed gas of carbon dioxide with air, steam-containing inert gas and the like in view of ease of availability and economical efficiency. In the case of applying the above-mentioned inactivation method to the conventional process using potassium, sodium or an alloy thereof as a catalyst for alkenylation reaction, there is a danger that fire would break out because of a large amount of reaction heat. Thus, it is made necessary to dilute the gas with a large amount of an inert gas such as nitrogen, helium or argon or to take a countermeasure such as a delicate control of the gas feed rate. On the other hand, the use of the alkali metal-based catalyst supported on a carrier as in the present invention can make relatively low the rate of reaction of the supported catalyst with air, oxygen or steam, and make it not always necessary to carry out a troublesome operation such as the delicate control of the gas feed rate. The simplified and advantageous handling in the present invention is due to the reactivity of the alkali metal supported on a carrier.

The period of time of contact between the reaction liquid and the gas is not specifically limited, but may only be the period of time sufficient to inactivate the active alkali metal-based catalyst supported on a carrier. The contact temperature can be selected in a wide range from room temperature to the boiling point of the aromatic hydrocarbon compound as the starting raw material, but room temperature is usually sufficient.

The contact method is selected from a batchwise system, semi-batchwise a system, complete a mixing flow system and the like. Any of the aforesaid system is acceptable insofar as the gas-liquid contact is sufficient.

In the case where the alkali metal components can not perfectly be removed by a method in which the active alkali metal-based catalyst supported on a carrier is inactivated by bringing the aforesaid gas into contact with the reaction liquid and the remaining catalyst in the form of fine grains is further removed by the use of a filter or the like, there may be used in combination therewith a method in which the reaction liquid is washed with a liquid such as water, aqueous solution of an acid, alcohol or the like as mentioned hereinafter, and/or a method in which the alkali metal-based catalyst supported on a carrier is removed by inactivating the same by means of a solid such as the aforestated solid acid, carbonaceous material, cationic ion exchange resin or the like.

In the present invention, the catalyst can be inactivated and/or removed by bringing the reaction liquid from which at least a part of catalyst in it has been removed into contact with at least one member selected from the group consisting of water and an aqueous solution of an acid; with an alcohol and thereafter with at least one member selected from the group consisting of water and an aqueous solution of acid; or with an alcohol and thereafter with at least one member selected from the group consisting of solid acid, carbonaceous material and cationic ion exchange resin.

The method in which a liquid such as water, an aqueous acid solution, alcohol or the like is employed is to inactivate the catalyst by converting the free alkali metal in the active alkali metal-based catalyst supported on a carrier into an alkoxide, hydroxide or salt through mixing of the reaction liquid with the liquid. Of the method using liquid, the preferable method is that using water or aqueous an solution of an acid.

In the case of applying the aforesaid method using water or aqueous an solution of an acid to the conventional process using potassium, sodium or an alloy thereof as a catalyst for alkenylation reaction, there is a danger that a large amount of reaction heat is generated at the time of inactivation, whereby fire would break out. Hence it is made necessary to preliminarily inactivate the catalyst by bringing the reaction liquid into contact in advance with an alcohol, a gas such as carbon dioxide or a solid such as a solid acid. On the other hand, the use of the alkali metal-based catalyst supported on a carrier as in the present invention makes it not always necessary to perform such preliminary treatment and facilitates the handling. This is due to the reactivity of the alkali metal supported on a carrier. The inactivation reaction can be controlled by regulating the feed rate of the reaction liquid, and a high feed rate can be selected in the present invention as compared with the conventional process using potassium, sodium or an alloy thereof as a catalyst.

The above-mentioned aqueous solution of an acid is not specifically limited, but may be an inorganic acid such as hydrochloric acid, sulfuric acid, nitric acid, phosphoric acid and aqueous solution of an organic acid such as formic acid, acetic acid, butyric acid and benzoic acid. When such aqueous solution of an acid is brought into contact with the reaction liquid, separation into two layers takes place, thereby separating the alkali metal components in the alkali metal-based catalyst supported on a carrier inactivated by the acid into the water layer as aqueous solution of alkali salt. The amount of aqueous solution of an acid to be used is not specifically limited, but may be an amount sufficient for removing the alkali metal components. In the case of bringing the reaction liquid into contact with a water-free acid or an organic acid as such that is soluble in organic solvent, a side reaction of a monoalkenyl aromatic hydrocarbon compound unfavorably occurs by the presence of the acid catalyst in the distillation step, if an excess acid remains in the reaction liquid.

When water is brought into contact with the reaction liquid, separation into two layers takes place, thereby extracting the alkali metal components in the inactivated catalyst into the water layer as an alkali metal hydroxide. The amount of water to be used is not specifically limited, but may be an amount sufficient for removing the alkali metal components.

The period of time of contact between the reaction liquid and the liquid is not specifically limited, but may only be the period of time sufficient to inactivate the active alkali metal-based catalyst supported on a carrier. The contact temperature can be selected in a wide range from room temperature to the boiling point of the aromatic hydrocarbon compound as the starting raw material, but room temperature is usually sufficient.

The contact method is selected from a batchwise system, a semi-batchwise system, a complete mixing flow system and the like. Any of the aforesaid systems is acceptable insofar as the liquid-liquid contact is sufficient.

When the aqueous solution of an acid and/or water come into contact with the reaction liquid, most of the fine grains in the reaction liquid and the alkali metal components are transferred to the water layer, hardly remaining in the oil layer. However, inactivation and/or removal of the catalyst can be carried out more effectively by bringing the reaction liquid into contact further with the solid such as solid acid, carbonaceous material or cationic ion exchange resin as described hereinbefore.

The alcohol usable for inactivating the catalyst by converting the alkali metal components in the alkali metal-based catalyst supported on a carrier into an alkali alkoxide through contact with the reaction liquid is not specifically limited provided that there is much difference in boiling point between the alcohol and the objective monoalkenyl aromatic hydrocarbon compound, but is exemplified preferably by methanol, ethanol, propanol, isopropanol and butanol, of which isopropanol and the like are particularly preferable from the viewpoint of reactivity and safety.

When active alkali metal-based catalyst supported on a carrier is brought into contact with an alcohol, the alkali metal components in the catalyst turn into alkali alcoholates, of which those beyond the solubility are precipitated as solid but soluble ones still remain in reaction liquid. In the case where the reaction liquid containing the soluble alkali alcoholate is introduced as such in a distillation column, where the unreacted aromatic hydrocarbon compound is distilled away, the alkali alcoholates beyond their solubility are precipitated as solid and accumulated in the column, therefore, it is necessary to remove the alkali alcoholate contained in the reaction liquid. The removal thereof can be put into practice more effectively by simultaneously using method in which the reaction liquid is brought into contact with the liquid such as water and an aqueous solution of an acid and the method in which the reaction liquid is brought into contact with the solid such as a solid acid, carbonaceous material and cationic ion exchange resin.

As described hereinbefore, the method in which a monoalkenyl aromatic hydrocarbon compound as the objective product is separated and recovered by distillating the reaction liquid containing the monoalkenyl aromatic hydrocarbon compound wherein the alkali metal-based catalyst supported on a carrier is inactivated and/or removed therefrom can prevent the change in quality and property of the objective product even during atmospheric distillation, produce the objective product with high purity in high recovery rate and operate a distillation column during a long stable period of time, thus rendering itself industrially significant to a great extent.

A monoalkenyl aromatic hydrocarbon compound is useful as the starting intermediate material for various organic compounds typified by high molecular monomers and pharmaceutical preparations. As an example, 5-(o-tolyl)-2-pentene that is produced from o-xylene and 1,3-butadiene can be converted into industrially useful 2,6-naphthalene-dicarboxylic acid by ring closure followed by dehydrogenation, isomerization and oxidation.

In the following, the present invention will be described in more detail with reference to non-limitative examples and comparative examples.

EXAMPLE 1

A solution of 2.09 kg of KOH in water was incorporated with 5.8 kg of powdery $Al_2O_3$ (DN-1, produced by Mizusawa Chemical Industries, Ltd.), followed by mixing at room temperature under stirring for one hour. After drying at 115° C., overnight, the mixture was calcined in the air at 550° C., The calcined mixture in an 500 g amount of was agitated in an atmosphere of nitrogen at 150° C., incorporated with 60 g of metallic Na and stirred at 150° C., for 30 minutes to prepare a powdery catalyst. Then 100 kg of o-xylene which had been dehydrated by means of a molecular sieve was incorporated with the resultant catalyst in a stream of nitrogen and heated to 140° C., Subsequently 7.0 kg of 1,3-butadiene was introduced into the o-xylene containing the catalyst under stirring and atmospheric pressure over a period of one (1) hour to proceed with alkenylation reaction.

After the completion of the reaction, stirring was stopped and the reaction liquid was allowed to stand and cool, taken out from the reaction system and sampled for analysis by gas chromatography. The analysis results are given in Table 1. As a result, 5-(o-tolyl)-2-pentene was obtained in a selectivity of 83.0% based on 1,3-butadiene.

The reaction liquid was passed through a fixed-bed type column packed inside with activated clay so that the alkali metal-based catalyst supported on the carrier was almost completely adsorbed onto the activated clay, inactivated and removed from the reaction liquid, and was further passed through a sintered metal filter made of stainless steel with pores of one (1) micron in diameter. Thereafter the reaction liquid thus treated was introduced into a recovery column for o-xylene at a feed rate of 10 kg/hr, which was operated under atmospheric pressure at a bottom temperature of 230° C., Table 2 gives the compositions and output rates for overhead liquid and bottom liquid. No change was observed in the properties of the objective 5-(o-tolyl)-2-pentene in the bottom liquid. Thereafter a refining column for 5-(o-tolyl)-2-pentene was operated under atmospheric pressure at a bottom temperature of 250° C. As a result, the objective 5-(o-tolyl)-2-pentene as the overhead product with 99.8% purity was obtained in 98.5% recovery rate.

EXAMPLE 2

The procedure in Example 1 was repeated except that the adsorption, inactivation and removal of the alkali metal-based catalyst supported on the carrier were carried out by the use of a hydrogen ion-type mordenite. As a result, 5-(o-tolyl)-2-pentene with 99.7% purity was obtained in 98.4% recovery rate.

EXAMPLE 3

The procedure in Example 1 was repeated except that the adsorption, inactivation and removal of the alkali metal-based catalyst supported on the carrier were carried out by the use of activated carbon. As a result, 5-(o-tolyl)-2-pentene with 99.6% purity was obtained in 98.4% recovery rate.

EXAMPLE 4

The procedure in Example 1 was repeated except that the adsorption, inactivation and removal of the alkali metal-based catalyst supported on the carrier were carried out by the use of graphite. As a result, 5-(o-tolyl)-2-pentene with 99.6% purity was obtained in 98.8% recovery rate.

EXAMPLE 5

The procedure in Example 1 was repeated except that the adsorption, inactivation and removal of the alkali metal-based catalyst supported on the carrier were carried out by the use of a sulfonic acid-based ion exchange resin (Amberlist 15). As a result, 5-(o-tolyl)-2-pentene with 99.6% purity was obtained in 98.9% recovery tale.

EXAMPLE 6

The procedure in Example 1 was repeated except that the carrier was prepared by adding 5.8 kg of CaO to a solution of 2.09 kg of KOH in water, mixing the mixture at room temperature under stirring for one hour, drying the mixture at 115° C., overnight and calcining the dried product in the air at 500° C. As a result, 5-(o-tolyl)-2-pentene with 99.5% purity was obtained in 98.3% recovery rate.

EXAMPLE 7

The procedure in Example 1 was repeated except that the carrier was prepared by adding 5.8 kg of $ZrO_2$ to a solution of 2.09 kg of KOH in water, mixing the mixture at room temperature under stirring for one hour, drying the mixture at 115° C., overnight and calcining the dried product in the air at 500° C. As a result, 5-(o-tolyl)-2-pentene with 99.8% purity was obtained in 98.1% recovery rate.

EXAMPLE 8

The procedure in Example 7 was repeated except that the reaction liquid which had been passed through the fixed-bed type column packed inside with activated clay was directly introduced into the recovery column without further being passed through the sintered metal filter. As a result, 5-(o-tolyl)-2-pentene with 99.7% purity was obtained in 98.4% recovery rate.

Comparative Example 1

The procedure in Example 1 was repeated except that the reaction liquid was directly introduced into the recovery column without being passed through the fixed-bed type column and the sintered metal filter. Table 2 gives the composition and output rate for overhead liquid and bottom liquid. There were observed a change in the properties of the objective 5-(o-tolyl)-2-pentene in the bottom liquid, high boiling components due to further reaction of 5-(o-tolyl)-2-pentene with o-xylene, an increase in the amount of o-xylene due to the reverse reaction of alkenylation reaction and the isomers containing 5-(o-tolyl)-3-pentene and 5-(o-tolyl)-4-pentene that were formed by the transfer of the double bond of 5-(o-tolyl)-2-pentene.

Comparative Example 2

The reaction liquid taken out from the reaction system in the same manner as in Example 1 was passed through the sintered metal filter made of stainless steel with pores of one (1) micron in diameter and, without being subjected to catalyst inactivation, was introduced into a recovery column for o-xylene at a feed rate of 10 kg/hr, which was operated under a reduced pressure of 20 mmHg at a bottom temperature of 120° C. Table 2 gives the compositions and output rates for overhead liquid and bottom liquid after one-day operation of the recovery column. As a result, the change in the properties of 5-(o-tolyl)-2-pentene decreased as compared with Comparative Example 1, but it was impossible to suppress the formation of byproducts.

Comparative Example 3

The procedure in Comparative Example 2 was repeated except that the recovery column was operated for 5 days. The results are given also in Table 2. The change in the properties of 5-(o-tolyl)-2-pentene increased. The alkali metal-based catalyst was concentrated in the distillation column, thereby making it impossible to decrease the change in the properties of 5-(o-tolyl)-2-pentene and purify the product at a high recovery rate by regulating only the operational conditions of the distillation column. The operation of the recovery column was continued, but after the lapse of 9 days, precipitation of solid took place around the feed plate of the column, whereby the feeding of the reaction liquid was made difficult and the operation was discontinued.

TABLE 1

| | |
|---|---|
| o-Xylene | 81.87 wt% |
| OTP-2 | 16.10 wt% |
| OTP-3 | 0.003 wt% |
| OTP-4 | 0.016 wt% |
| C20H | 0.071 wt% |
| Other high boiling byproducts | 2.03 wt% |

OTP-2: 5-(o-tolyl)-2-pentene
OTP-3: 5-(o-tolyl)-3-pentene
OTP-4: 5-(o-tolyl)-4-pentene
C20H: Reaction product having 266 molecular weight between 5-(o-tolyl)-2-pentene and o-xylene

TABLE 2

| | Example 1 | Comparative 1 | Comparative 2 | Comparative 3 |
|---|---|---|---|---|
| Overhead liquid | | | | |
| Output rate kg/hr | 8.19 | 8.28 | 8.21 | 8.31 |
| Composition, wt % | | | | |
| o-Xylene | 99.99 | 99.99 | 99.99 | 99.99 |
| OTP-2 | 0.001 | 0.001 | 0.001 | 0.001 |
| Bottom liquid | | | | |
| Output rate kg/hr | 1.81 | 1.72 | 1.79 | 1.69 |
| Composition, wt % | | | | |
| o-Xylene | 0.001 | 0.001 | 0.001 | 0.001 |
| OTP-2 | 88.36 | 71.46 | 85.43 | 60.45 |
| OTP-3 | 0.015 | 0.71 | 0.14 | 0.83 |
| OTP-4 | 0.088 | 4.73 | 0.95 | 6.28 |
| C20H | 0.39 | 2.67 | 0.53 | 4.06 |
| Other high boiling byproduct | 11.15 | 20.42 | 12.95 | 28.38 |

EXAMPLE 9

The procedure in Example 1 was repeated except that the inactivation of the alkali metal-based catalyst supported on the carrier was carried out by allowing air to bubble in the reaction liquid in place of adsorption onto activated clay. As a result, 5-(o-tolyl)-2-pentene with 99.8% purity was obtained in 98.5% recovery rate.

EXAMPLE 10

The procedure in Example 9 was repeated except that the inactivation of the alkali metal-based catalyst supported on the carrier was carried out by the use of steam diluted with nitrogen in place of bubbling air. As a result, 5-(o-tolyl)-2-pentene with 99.7% purity was obtained in 98.4% recovery rate.

EXAMPLE 11

The procedure in Example 9 was repeated except that the inactivation of the alkali metal-based catalyst supported on the carrier was carried out by the use of mixed gas of carbon dioxide with air in place of bubbling air. As a result, 5-(o-tolyl)-2-pentene with 99.6% purity was obtained in 98.3% recovery rate.

EXAMPLE 12

The procedure in Example 9 was repeated except that the carrier was prepared by adding 5.8 kg of CaO to a solution of 2.09 kg of KOH in water, mixing the mixture at room temperature under stirring for one hour, drying the mixture at 115° C., overnight and calcining the dried product in the air at 500° C. As a result, 5-(o-tolyl)-2-pentene with 99.5% purity was obtained in 98.3% recovery rate.

EXAMPLE 13

The procedure in Example 9 was repeated except that the carrier was prepared by adding 5.8 kg of $ZrO_2$ to a solution of 2.09 kg of KOH in water, mixing the mixture at room temperature under stirring for one hour, drying the mixture at 115° C., overnight and calcining the dried product in the air at 500° C. As a result, 5-(o-tolyl)-2-pentene with 99.8% purity was obtained in 98.1% recovery rate.

EXAMPLE 14

The procedure in Example 1 was repeated except that the reaction liquid which had been taken out from the reaction system was incorporated with water with stirring to completely inactivate the catalyst, allowed to stand to separate into an oil layer and a water layer and to remove the alkali metal components into the water layer. The reaction liquid as the oil layer was passed through a sintered metal filter made of stainless steel with pores of one (1) micron in diameter to remove the remaining solids and thereafter introduced into the recovery column for o-xylene. As the result, 5-(o-tolyl)-2-pentene with 99.8% purity was obtained in 98.5% recovery rate.

EXAMPLE 15

The procedure in Example 14 was repeated except that the inactivation of the alkali metal-based catalyst supported on the carrier was carried out by the use of 2% aqueous solution of acetic acid. As a result, 5-(o-tolyl)-2-pentene with 99.7% purity was obtained in 98.4% recovery rate.

EXAMPLE 16

The procedure in Example 14 was repeated except that the inactivation of the alkali metal-based catalyst supported on the carrier was carried out by the use of 1% aqueous solution of hydrochloric acid and the filtration with the sintered metal filter was omitted. As a result, 5-(o-tolyl)-2-pentene with 99.6% purity was obtained in 8.5% recovery rate.

EXAMPLE 17

The procedure in Example 16 was repeated except that the inactivation of the alkali metal-based catalyst supported on the carrier was completely carried out by the use of isopropanol, and alkali metal components were removed totally in the water layer by bringing the reaction liquid into contact with water. As a result, 5-(o-tolyl)-2-pentene with 99.5% purity was obtained in 98.5% recovery rate.

EXAMPLE 18

The procedure in Example 16 was repeated except that the inactivation of the alkali metal-based catalyst supported on the carrier was completely carried out by the use of isopropanol, and alkali metal components were removed totally onto the solid by bringing the reaction liquid into contact with activated clay. As a result, 5-(o-tolyl)-2-pentene with 99.5% purity was obtained in 98.5% recovery rate.

EXAMPLE 19

The procedure in Example 16 was repeated except that the carrier was prepared by adding 5.8 kg of CaO to a solution of 2.09 kg of KOH in water, mixing the mixture at room temperature under stirring for one hour, drying the mixture at 115° C., overnight and calcining the dried product in the air at 500° C. As a result, 5-(o-tolyl)-2-pentene with 99.5% purity was obtained in 98.3% recovery rate.

EXAMPLE 20

The procedure in example 16 was repeated except that the carrier was prepared by adding 5.8 kg of $ZrO_2$ to a solution of 2.09 kg of KOH in water, mixing the mixture at room temperature under stirring for one hour, drying the mixture at 115° C., overnight and calcining the dried product in the air at 500° C. As a result, 5-(o-tolyl)-2-pentene with 99.8% purity was obtained in 98.1% recovery rate.

What is claimed is:

1. A process for producing a monoalkenyl aromatic hydrocarbon compound which comprises
   (a) alkenylating a side chain of an aromatic hydrocarbon compound having at least one hydrogen atom bonded to an α-position of the side chain with a conjugated diene having 4 to 5 carbon atoms in the presence of an alkali metal-based catalyst supported on a carrier, said carrier being selected from the group consisting of (i) a carrier obtained by calcining a mixture of potassium hydroxide and aluminum hydroxide at 400° to 700° C., (ii) a carrier obtained by calcining a mixture of a basic potassium compound and alumina at 500° to 700° C., (iii) an alkaline earth metal oxide carrier containing a potassium compound, and (iv) a zirconium oxide carrier containing a potassium compound and heating the mixture at 100° to 300° C., in inert gas;
   (b) removing at least part of said catalyst from the resultant reaction product by separating the same;
   (c) inactivating or, inactivating and removing, the catalyst contained in the reaction product by contacting the reaction product with at least one member selected from the group consisting of a solid acid, a carbonaceous material and a cationic ion exchange resin, said solid acid being selected from the group consisting of activated clay, alumina, silica-alumina and a zeolite, said carbonaceous material being selected from the group consisting of graphite, activated carbon, a PAN-based carbon fiber and amorphous carbon obtained by baking a petroleum-based or a coal-based pitch; and
   (d) thereafter distilling the reaction product in liquid form to separate and recover the monoalkenyl aromatic hydrocarbon compound.

2. The process according to claim 1 wherein the aromatic hydrocarbon compound having at least one hydrogen atom bonded to an α-position of the side chain is an alkylbenzene.

3. The process according to claim 1 which further comprises the step of filtering the reaction product by the use of a filter having a pore size of 5 micron or smaller after the step of inactivating or, inactivating and removing, the catalyst contained in the reaction product.

4. A process for producing a monoalkenyl aromatic hydrocarbon compound which comprises
   (a) alkenylating a side chain of an aromatic hydrocarbon compound having at least one hydrogen atom bonded to an α-position of the side chain with a conjugated diene having 4 to 5 carbon atoms in the presence of an alkali metal-based catalyst supported on a carrier, said carrier being selected from the group consisting of (i) a carrier obtained by calcining a mixture of potassium hydroxide and aluminum hydroxide at 400° to 700° C., (ii) a carrier obtained by calcining a mixture of a basic potassium compound and alumina at 500° to 700° C., (iii) an alkaline earth metal oxide carrier containing a potassium compound, and (iv) a zirconium oxide carrier containing a potassium compound and heating the mixture at 100° to 300° C., in inert gas;
   (b) removing at least part of said catalyst from the resultant reaction product by separating the same;
   (c) inactivating or, inactivating and removing, the catalyst contained in the reaction product by contacting the reaction product with at least one member selected from the group consisting of air, oxygen and steam; and
   (d) thereafter distilling the reaction product in liquid form to separate and recover the monoalkenyl aromatic hydrocarbon compound.

5. A process for producing a monoalkenyl aromatic hydrocarbon compound which comprises
   (a) alkenylating a side chain of an aromatic hydrocarbon compound having at least one hydrogen atom bonded to an α-position of the side chain with a conjugated diene having 4 to 5 carbon atoms in the presence of an alkali metal-based catalyst supported on a carrier, said carrier being selected from the group consisting of (i) a carrier obtained by calcining a mixture of potassium hydroxide and aluminum hydroxide at 400° to 700° C., (ii) a carrier obtained by calcining a mixture of a basic potassium compound and alumina at 500° to 700° C., (iii) an alkaline earth metal oxide carrier containing a potassium compound, and (iv) a zirconium oxide carrier containing a potassium compound and heating the mixture at 100° to 300° C., in inert gas;
   (b) removing at least part of said catalyst from the resultant reaction product by separating the same;
   (c) inactivating or, inactivating and removing, the catalyst contained in the reaction product by contacting the reaction product with a mixed gas of at least one member selected from the group consisting of oxygen and steam, with a diluting inert gas; and
   (d) thereafter distilling the reaction product in liquid form to separate and recover the monoalkenyl aromatic hydrocarbon compound.

6. A process for producing a monoalkenyl aromatic hydrocarbon compound which comprises
   (a) alkenylating a side chain of an aromatic hydrocarbon compound having at least one hydrogen atom bonded to an α-position of the side chain with a conjugated diene having 4 to 5 carbon atoms in the presence of an alkali metal-based catalyst supported on a carrier, said carrier being selected from the group consisting of (i) a carrier obtained by calcining a mixture of potassium hydroxide and aluminum hydroxide at 400° to 700° C., (ii) a carrier obtained by calcining a mixture of a basic potassium compound and alumina at 500° to 700° C., (iii) an alkaline earth metal oxide carrier containing a potassium compound, and (iv) a zirconium oxide carrier containing a potassium compound and heating the mixture at 100° to 300° C., in inert gas;
   (b) removing at least part of said catalyst from the resultant reaction product by separating the same;
   (c) inactivating or, inactivating and removing, the catalyst contained in the reaction product by contacting the reaction product with at least one member selected from the group consisting of water and a solution of an acid in water; and
   (d) thereafter distilling the reaction product in liquid form to separate and recover the monoalkenyl aromatic hydrocarbon compound.

7. A process for producing a monoalkenyl aromatic hydrocarbon compound which comprises
   (a) alkenylating a side chain of an aromatic hydrocarbon compound having at least one hydrogen atom bonded to an α-position of the side chain with a conjugated diene having 4 to 5 carbon atoms in the presence of an alkali metal-based catalyst supported on a carrier, said carrier being selected from the group consisting of (i) a carrier obtained by calcining a mixture of potassium hydroxide and aluminum hydroxide at 400° to 700° C., (ii) a carrier obtained by calcining a mixture of a basic potassium compound and alumina at 500° to 700° C., (iii) an alkaline earth metal oxide carrier containing a potassium compound, and (iv) a zirconium oxide carrier containing a potassium compound and heating the mixture at 100° to 300° C., in inert gas;
   (b) removing at least part of said catalyst from the resultant reaction product by separating the same;
   (c) inactivating or, inactivating and removing, the catalyst contained in the reaction product by contacting the reaction product with an alcohol and thereafter with at least one member selected from the group consisting of water and a solution of an acid in water; and
   (d) thereafter distilling the reaction product in liquid form to separate and recover the monoalkenyl aromatic hydrocarbon compound.

8. A process for producing a monoalkenyl aromatic hydrocarbon compound which comprises
   (a) alkenylating a side chain of an aromatic hydrocarbon compound having at least one hydrogen atom bonded to an α-position of the side chain with a conjugated diene having 4 to 5 carbon atoms in the presence of an alkali metal-based catalyst supported on a carrier, said carrier being selected from the group consisting of (i) a carrier obtained by calcining a mixture of potassium hydroxide and aluminum hydroxide at 400° to 700° C., (ii) a carrier obtained by calcining a mixture of a basic potassium compound and alumina at 500° to 700° C., (iii) an alkaline earth metal oxide carrier containing a potassium compound, and (iv) a zirconium oxide carrier containing a potassium compound and heating the mixture at 100° to 300° C., in inert gas;
   (b) removing at least part of said catalyst from the resultant reaction product by separating the same;
   (c) inactivating or, inactivating and removing the catalyst contained in the reaction product by contacting the reaction product with an alcohol and thereafter with at least one member selected from the group consisting of a solid acid, a carbonaceous material and a cationic ion exchange resin, said solid acid being selected from the group consisting of activated clay, alumina, silica-alumina and a zeolite, said carbonaceous material being selected from the group consisting of graphite, activated carbon, a PAN-based carbon fiber and amorphous carbon obtained by baking a petroleum-based or a coal-based pitch; and (d) thereafter distilling the reaction product in liquid form to separate and recover the monoalkenyl aromatic hydrocarbon compound.

9. The process according to claim 1 wherein the alkali metal-based catalyst supported on a carrier is a mixture obtained by calcining a mixture of potassium hydroxide and aluminum hydroxide at a temperature of 400° to 700° C. adding metallic sodium to the resultant calcined product in an atmosphere of an inert gas, and heat treating the mixture at a temperature of 100° to 300° C.

10. The process according to claim 1 wherein the alkali metal-based catalyst supported on a carrier is a mixture obtained by calcining a mixture of a basic potassium compound and alumina at a temperature of 500° to 700° C. adding metallic sodium to the resultant calcined product in an atmosphere of an inert gas, and heat treating the mixture at a temperature of 100° to 300° C., 11. The process according to claim 1 wherein the alkali metal-based catalyst supported on a carrier is a mixture obtained by heat treating an alkaline earth metal oxide containing a potassium compound along with metallic sodium in an atmosphere of an inert gas.

12. The process according to claim 1 wherein the alkali metal-based catalyst supported on a carrier is a mixture obtained by heat treating zirconium oxide containing a potassium compound along with metallic sodium in an atmosphere of an inert gas.

13. The process according to claim 4 wherein the aromatic hydrocarbon compound having at least one hydrogen atom bonded to an α-position of the side chain is an alkylbenzene.

14. The process according to claim 4 which further comprises filtering the reaction product by the use of a filter having a pore size of 5 microns or smaller, after the step of inactivating or, inactivating and removing, the catalyst contained in the reaction product.

15. The process according to claim 4 wherein the alkali metal-based catalyst supported on a carrier is a mixture obtained by calcining a mixture of potassium hydroxide and aluminum hydroxide at a temperature of 400° to 700° C., adding metallic sodium to the resultant calcined product in an atmosphere of an inert gas, and heat treating the mixture at a temperature of 100° to 300° C.

16. The process according to claim 4 wherein the alkali metal-based catalyst supported on a carrier is a mixture obtained by calcining a mixture of a basic potassium compound and alumina at a temperature of 500° to 700° C., adding metallic sodium to the resultant calcined product in an atmosphere of an inert gas, and heat treating the mixture at a temperature of 100° to 300° C.

17. The process according to claim 4 wherein the alkali metal-based catalyst supported on a carrier is a mixture obtained by heat treating an alkaline earth metal oxide containing a potassium compound along with metallic sodium in an atmosphere of an inert gas.

18. The process according to claim 4 wherein the alkali metal-based catalyst supported on a carrier is a mixture obtained by heat treating zirconium oxide containing a potassium compound along with metallic sodium in an atmosphere of an inert gas.

19. The process according to claim 5 wherein the aromatic hydrocarbon compound having at least one hydrogen atom bonded to an α-position of the side chain is an alkylbenzene.

20. The process according to claim 5 which further comprises filtering the reaction product by the use of a filter having a pore size of 5 microns or smaller, after the step of inactivating or, inactivating and removing, the catalyst contained in the reaction product.

21. The process according to claim 5 wherein the alkali metal-based catalyst supported on a carrier is a mixture obtained by calcining a mixture of potassium hydroxide and aluminum hydroxide at a temperature of 400° to 700° C., adding metallic sodium to the resultant calcined product in an atmosphere of an inert gas, and heat treating the mixture at a temperature of 100° to 300° C.

22. The process according to claim 5 wherein the alkali metal-based catalyst supported on a carrier is a mixture obtained by calcining a mixture of a basic potassium compound and alumina at a temperature of 500° to 700° C., adding metallic sodium to the resultant calcined product in an atmosphere of an inert gas, and heat treating the mixture at a temperature of 100° to 300° C.

23. The process according to claim 5 wherein the alkali metal-based catalyst supported on a carrier is a mixture obtained by heat treating an alkaline earth metal oxide containing a potassium compound along with metallic sodium in an atmosphere of an inert gas.

24. The process according to claim 5 wherein the alkali metal-based catalyst supported on a carrier is a mixture obtained by heat treating zirconium oxide containing a potassium compound along with metallic sodium in an atmosphere of an inert gas.

25. The process according to claim 6 wherein the aromatic hydrocarbon compound having at least one hydrogen atom bonded to an α-position of the side chain is an alkylbenzene.

26. The process according to claim 6 which further comprises of filtering the reaction product by the use of a filter having a pore size of 5 microns or smaller, after the step of inactivating or, inactivating and removing, the catalyst contained in the reaction product.

27. The process according to claim 6 wherein the alkali metal-based catalyst supported on a carrier is a mixture obtained by calcining a mixture of potassium hydroxide and aluminum hydroxide at a temperature of 400° to 700° C., adding metallic sodium to the resultant calcined product in an atmosphere of an inert gas, and heat treating the mixture at a temperature of 100° to 300° C.

28. The process according to claim 6 wherein the alkali metal-based catalyst supported on a carrier is a mixture obtained by calcining a mixture of a basic potassium compound and alumina at a temperature of 500° to 700° C., adding metallic sodium to the resultant calcined product in an atmosphere of an inert gas, and heat treating the mixture at a temperature of 100° to 300° C.

29. The process according to claim 6 wherein the alkali metal-based catalyst supported on a carrier is a mixture obtained by heat treating an alkaline earth metal oxide containing a potassium compound along with metallic sodium in an atmosphere of an inert gas.

30. The process according to claim 6 wherein the alkali metal-based catalyst supported on a carrier is a mixture obtained by heat treating zirconium oxide containing a potassium compound along with metallic sodium in an atmosphere of an inert gas.

31. The process according to claim 7 wherein the aromatic hydrocarbon compound having at least one hydrogen atom bonded to an α-position of the side chain is an alkylbenzene.

32. The process according to claim 7 which further comprises filtering the reaction product by the use of a filter having a pore size of 5 microns or smaller, after the step of inactivating or, inactivating and removing, the catalyst contained in the reaction product.

33. The process according to claim 7 wherein the alkali metal-based catalyst supported on a carrier is a mixture obtained by calcining a mixture of potassium hydroxide and aluminum hydroxide at a temperature of 400° to 700° C., adding metallic sodium to the resultant calcined product in an atmosphere of an inert gas, and heat treating the mixture at a temperature of 100° to 300° C.

34. The process according to claim 7 wherein the alkali metal-based catalyst supported on a carrier is a mixture obtained by calcining a mixture of a basic potassium compound and alumina at a temperature of 500° to 700° C., adding metallic sodium to the resultant calcined product in an atmosphere of an inert gas, and heat treating the mixture at a temperature of 100° to 300° C.

35. The process according to claim 7 wherein the alkali metal-based catalyst supported on a carrier is a mixture obtained by heat treating an alkaline earth metal oxide containing a potassium compound along with metallic sodium in an atmosphere of an inert gas.

36. The process according to claim 7 wherein the alkali metal-based catalyst supported on a carrier is a mixture obtained by heat treating zirconium oxide containing a potassium compound along with metallic sodium in an atmosphere of an inert gas.

37. The process according to claim 8 wherein the aromatic hydrocarbon compound having at least one hydrogen atom bonded to an α-position of the side chain is an alkylbenzene.

38. The process according to claim 8 which further comprises filtering the reaction product by the use of a filter having a pore size of 5 microns or smaller, after the step of inactivating or, inactivating and removing, the catalyst contained in the reaction product.

39. The process according to claim 8 wherein the alkali metal-based catalyst supported on a carrier is a mixture obtained by calcining a mixture of potassium hydroxide and aluminum hydroxide at a temperature of 400° to 700° C., adding metallic sodium to the resultant calcined product in an atmosphere of an inert gas, and heat treating the mixture at a temperature of 100° to 300° C.

40. The process according to claim 8 wherein the alkali metal-based catalyst supported on a carrier is a mixture obtained by calcining a mixture of a basic potassium compound and alumina at a temperature of 500° to 700° C., adding metallic sodium to the resultant calcined product in an atmosphere of an inert gas, and heat treating the mixture at a temperature of 100° to 300° C.

41. The process according to claim 8 wherein the alkali metal-based catalyst supported on a carrier is a mixture obtained by heat treating an alkaline earth metal oxide containing a potassium compound along with metallic sodium in an atmosphere of an inert gas.

42. The process according to claim 8 wherein the alkali metal-based catalyst supported on a carrier is a mixture obtained by heat treating zirconium oxide containing a potassium compound along with metallic sodium in an atmosphere of an inert gas.

* * * * *